(12) United States Patent
Hoffman (10) Patent No.: US 9,717,869 B2
(45) Date of Patent: Aug. 1, 2017

(54) MODULAR CPAP COMPRESSOR (71) Applicant: CareFusion 212, LLC, San Diego, CA (US)

(72) Inventor: Leslie Hoffman, Tarzana, CA (US)

(73) Assignee: CAREFUSION 212, LLC, San Diego, CA (US)

( * ) Notice: Subject to any disclaimer, the term of this patent is extended or adjusted under 35 U.S.C. 154(b) by 392 days.

(21) Appl. No.: 14/256,875

(22) Filed: Apr. 18, 2014

(65) Prior Publication Data

US 2014/0223725 A1 Aug. 14, 2014

Related U.S. Application Data (62) Division of application No. 11/818,346, filed on Jun. 14, 2007, now Pat. No. 8,708,674.

(51) Int. Cl.
*A61M 16/00* (2006.01)
*F04D 29/40* (2006.01)

(52) U.S. Cl.
CPC .... *A61M 16/0063* (2014.02); *A61M 16/0066* (2013.01); *F04D 29/40* (2013.01); *A61M 2207/00* (2013.01); *Y10T 29/49012* (2015.01); *Y10T 29/49243* (2015.01)

(58) Field of Classification Search
CPC .......... A61M 16/0063; A61M 16/0066; A61M 2207/00; F04D 29/40; Y10T 29/49012; Y10T 29/49243
See application file for complete search history.

(56) References Cited

U.S. PATENT DOCUMENTS

| | | |
|---|---|---|
| 3,143,284 A | 8/1964 | Folke et al. |
| 3,543,368 A | 12/1970 | Marlow |
| 3,617,784 A | 11/1971 | Lindgren |
| 3,778,181 A | 12/1973 | McFarlin |
| 4,406,591 A | 9/1983 | Louis |
| 4,508,492 A | 4/1985 | Kusakawa et al. |
| 4,933,584 A | 6/1990 | Harms et al. |
| 5,480,268 A | 1/1996 | Smoot |
| 6,488,475 B2 | 12/2002 | Murata et al. |
| 6,604,906 B2 | 8/2003 | Ozeki et al. |
| 6,916,152 B2 | 7/2005 | Keener |
| 7,011,506 B2 | 3/2006 | Kim |
| 7,804,213 B2 * | 9/2010 | Hoffman .................. H02K 5/08 310/67 R |
| 2004/0071573 A1 | 4/2004 | Pfetzer et al. |
| 2004/0096345 A1 | 5/2004 | Zabar |

(Continued)

*Primary Examiner* — Richard Chang
(74) *Attorney, Agent, or Firm* — McDermott Will & Emery LLP (57) ABSTRACT

A modular compressor assembly comprises a common motor assembly, an impeller, a blower housing and an engagement mechanism. The common motor assembly includes a stator housing containing a stator assembly and having a rotor magnet rotatably disposed therewithin. The impeller is mounted to and rotatable with the rotor magnet. The blower housing is selectable from among a plurality of blower housings each having a different cross-sectional geometry. The engagement mechanism is formed on the stator housing and/or the blower housing and allows interchangeable mounting of different blower housing configurations to the common motor assembly in order to achieve varying flow characteristics of the compressor assembly.

9 Claims, 4 Drawing Sheets

(56) References Cited

U.S. PATENT DOCUMENTS

2005/0058556 A1 3/2005 Cremer et al.
2006/0093500 A1 5/2006 Liang
2006/0138878 A1 6/2006 Hoffman et al.
2007/0247009 A1 10/2007 Hoffman et al.

* cited by examiner

MODULAR CPAP COMPRESSOR

CROSS-REFERENCE TO RELATED APPLICATIONS

The present application is a divisional of U.S. patent application Ser. No. 11/818,346 entitled MODULAR CPAP COMPRESSOR filed Jun. 14, 2007, the entirety of the disclosure of which is expressly incorporated herein by reference for all purposes.

STATEMENT RE: FEDERALLY SPONSORED RESEARCH/DEVELOPMENT (Not Applicable)

BACKGROUND

The present invention relates generally to patient ventilation systems and, more particularly, to a modular compressor assembly which can be assembled using a baseline or common motor assembly to which can be mounted various sizes and configurations of blower housings in order to achieve different flow capabilities for the compressor assembly.

Blowers are commonly used in mechanical ventilators to generate compressed air for delivery to a patient. Such blower assemblies may comprise a blower housing having a blower inlet and a blower outlet. The blower assembly includes a motor assembly mounted within the blower housing and which is coupled to an impeller which draws air into the blower inlet. The air is compressed as it flows through the impeller and enters an annular chamber or volute after which the air is discharged from the blower outlet.

The motor assembly may be provided in a variety of alternative configurations such as a conventional brushed D.C. motor or in a brushless configuration. Because of their high operating efficiency under low-load conditions, brushless D.C. motors are particularly well-suited for use in generating compressed air. As such, brushless D.C. motors are commonly used in miniature fans and other blower configurations including certain ventilatory applications such as in CPAP devices for treating obstructed sleep apnea (OSA).

A further advantage of employing brushless D.C. motors in blower assemblies for CPAP devices is the reduced amount of vibration, heat and noise generated during operation which allows the use of CPAP devices in sensitive environments such as intensive care units (ICU) rooms or in a bedroom of a respiratory care patient. Furthermore, compressor assemblies powered by brushless D.C. motors may be packaged in very small sizes having low weight which, in association with their other advantages, makes them ideal for use in portable or wearable CPAP devices.

However, compressors used in CPAP therapy must be capable of generating different flow rates depending upon the type of respiratory treatment to be provided as well as the respiratory condition and physiological size of the patient. For example, patients undergoing CPAP treatment can range from pre-term infants, neonates and pediatric patients up to full-grown adult patients. As may be appreciated, the pressurized gas requirements of a neonatal patient differ markedly from the pressurized gas requirements of a full grown adult. Flow settings for neonates can be as low as 2 liters per minute (LPM) at pressures as low as 5 cm $H_2O$ as compared to the flow settings for a full grown adult patient requiring flow rates of up to 120 LPM and pressure settings of 20 cm $H_2O$ and higher.

As a result of these differing flow requirements, different compressor assemblies are designed for use with a certain range of flow settings. The compressor assemblies are optimized to produce the desired flow requirements at maximum operating efficiency and with minimal power consumption. In this regard, a common practice in the industry is to develop and manufacture a specific compressor assembly which produces optimal flow characteristics for a specific set of patient types and/or flow settings. As may be appreciated, the need to design, test and manufacture completely different configurations of compressor assemblies for different patients having differing flow requirements substantially increases the overall cost of CPAP devices.

As can be seen, there exists a need in the art for a compressor assembly having the capability to efficiently produce a broad range of flow characteristics (i.e., flow rate, pressure) for specific patient applications at a substantially reduced cost to the manufacturer and, ultimately, at a reduced cost to the consumer.

BRIEF SUMMARY

The above-mentioned needs associated with compressor assemblies having differing flow capabilities is specifically addressed by the present invention which provides a modular compressor assembly. The compressor assembly includes a baseline or common motor assembly having a preset or fixed configuration but which is mountable to blower housings of various configurations (e.g., different cross-sectional geometries) such that the compressor assembly may be used to provide a variety of different respiratory treatment modalities to patients of varying size. Advantageously, the interchangeability of the blower housing is facilitated by a universal engagement mechanism which conveniently and effectively allows for mounting of different blower housings on a single, common motor assembly.

In one embodiment, the motor assembly includes a stator housing containing a stator assembly. A rotor magnet is rotatably disposed within and coupled to the stator assembly. The compressor assembly further includes an impeller which may be selectable from among a plurality of impellers each having a different geometry and which is formed complimentary to the blower housing. The impeller is configured to be mountable to and rotatable in unison with the rotor magnet. The impeller rotates within the blower housing and draws air into the blower inlet after which the air is compressed and discharged at a blower outlet.

The blower housing may comprise upper and lower housing portions each configured to be engageable to one another at a perimeter joint such as by adhesive bonding, sonic welding or any other suitable means. At least one of the upper and lower housing portions includes the engagement mechanism to allow interchangeable mounting of the blower housing to the common motor assembly.

In one embodiment, the engagement mechanism may comprise a locating ring formed around an outer circumference of the gator housing. The lower housing portion may include a complimentary annular groove extending around an inner wall of the lower housing portion. The annular groove is preferably sized and configured complimentary to the locating ring such that the lower housing portion is maintained in fixed position relative to the motor assembly.

The motor assembly may be provided in any operational configuration but is preferably configured as a three-slot/two-pole brushless D.C. motor. The stator assembly preferably includes a stator bore for receiving the rotor magnet therewithin. The blower housing and stator housing collectively form an annular chamber or volute which defines a housing interior surface of the blower housing. The stator assembly includes a bearing assembly comprising upper and lower bearings disposed within the stator bore. The bearing assembly is configured to rotatably support the rotor magnet and the impeller relative to the stator assembly.

The impeller preferably includes a plurality of upwardly extending vanes each having a free edge defining a relatively small air gap with the housing interior surface. The impeller and bearing assembly are preferably sized and configured such that the air gap is maintained at a minimum (e.g., less than approximately 0.006 inches) during rotation of the impeller. In this manner, the compressor assembly minimizes aerodynamic losses such as vane-to-vane losses or losses resulting from parasitic fluid eddies which can reduce the operating efficiency of the compressor assembly.

BRIEF DESCRIPTION OF THE DRAWINGS

These and other features of the present invention will become more apparent upon reference to the drawings wherein.

DETAILED DESCRIPTION

Referring now to the drawings wherein the showings are for purposes of illustrating preferred embodiments of the present invention and not for purposes of limiting the same, shown in FIGS. 1 to 6 is a modular compressor assembly 10 which, in its broadest sense, comprises a baseline or common motor assembly 30 configured to be engageable to blower housings 12 of differing geometry to achieve differing flow characteristics using the same common motor assembly 30. Toward this end, the compressor assembly 10 includes an engagement mechanism 128 to allow for mounting of the motor assembly 30 to the blower housings 12.

In this manner, the compressor assembly 10 may be economically manufactured and capable of producing a broad range of flow characteristics (i.e., different flow rates and pressures) for specific patient applications at a substantially reduced cost. Advantageously, the common motor assembly 30 may include oversized bearings in order to maintain the operating efficiency of the compressor assembly 10 and to minimize vibration and/or noise regardless of the size of the impeller 56 or speed of rotation thereof.

Referring to FIGS. 1 to 6, shown is the modular compressor assembly 10 constructed in a manner such that the compressor assembly 10 has a relatively short axial length (i.e., short height) and relatively small overall diameter. The miniaturized or compact configuration of the compressor assembly 10 is due in part to the arrangement of the common motor assembly 30 which includes a stator housing 34 containing a stator assembly 32 and which includes a stator bore 38 formed therewithin. The common motor assembly 30 further includes a rotor magnet 106 disposed within the stator bore 38 and which is rotatably coupled to the stator assembly 32 by means of a pair of upper and lower bearings 88, 90.

Figure 1:
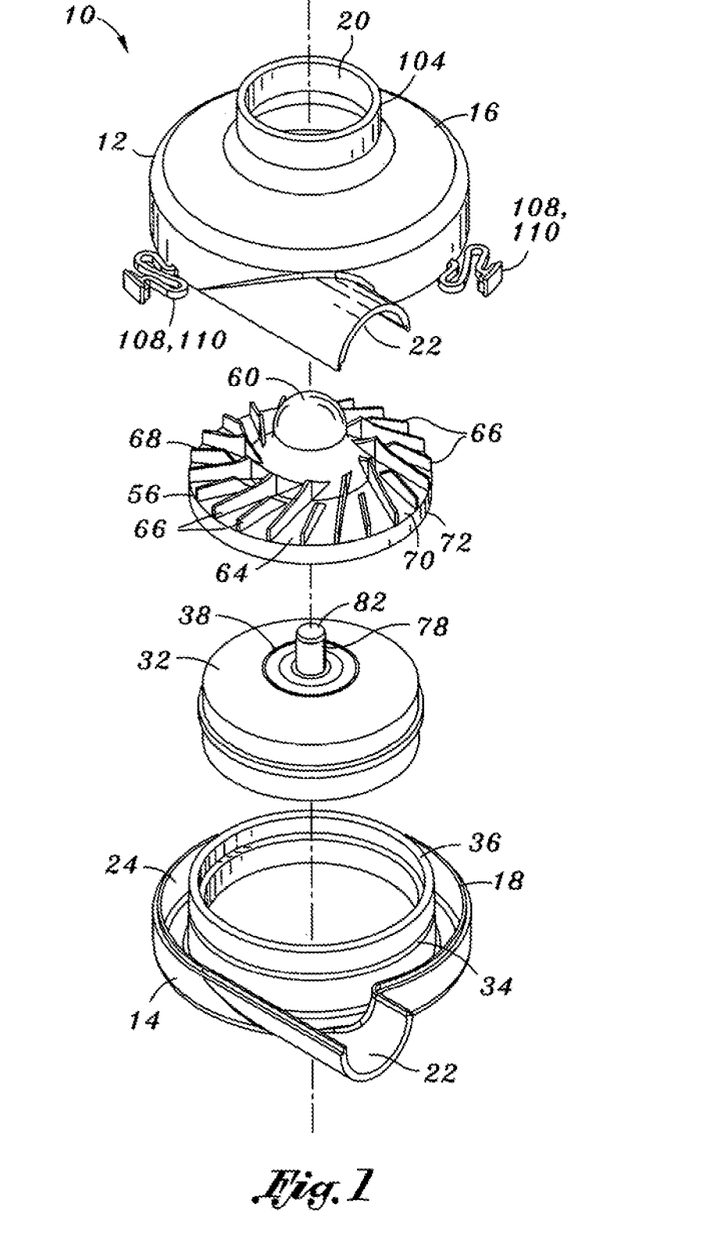
FIG. 1 is an exploded perspective view of a modular compressor assembly comprising a common motor assembly releasably engageable to a blower housing selectable from among a variety of blower housings each having a different configuration.
Figure 6:
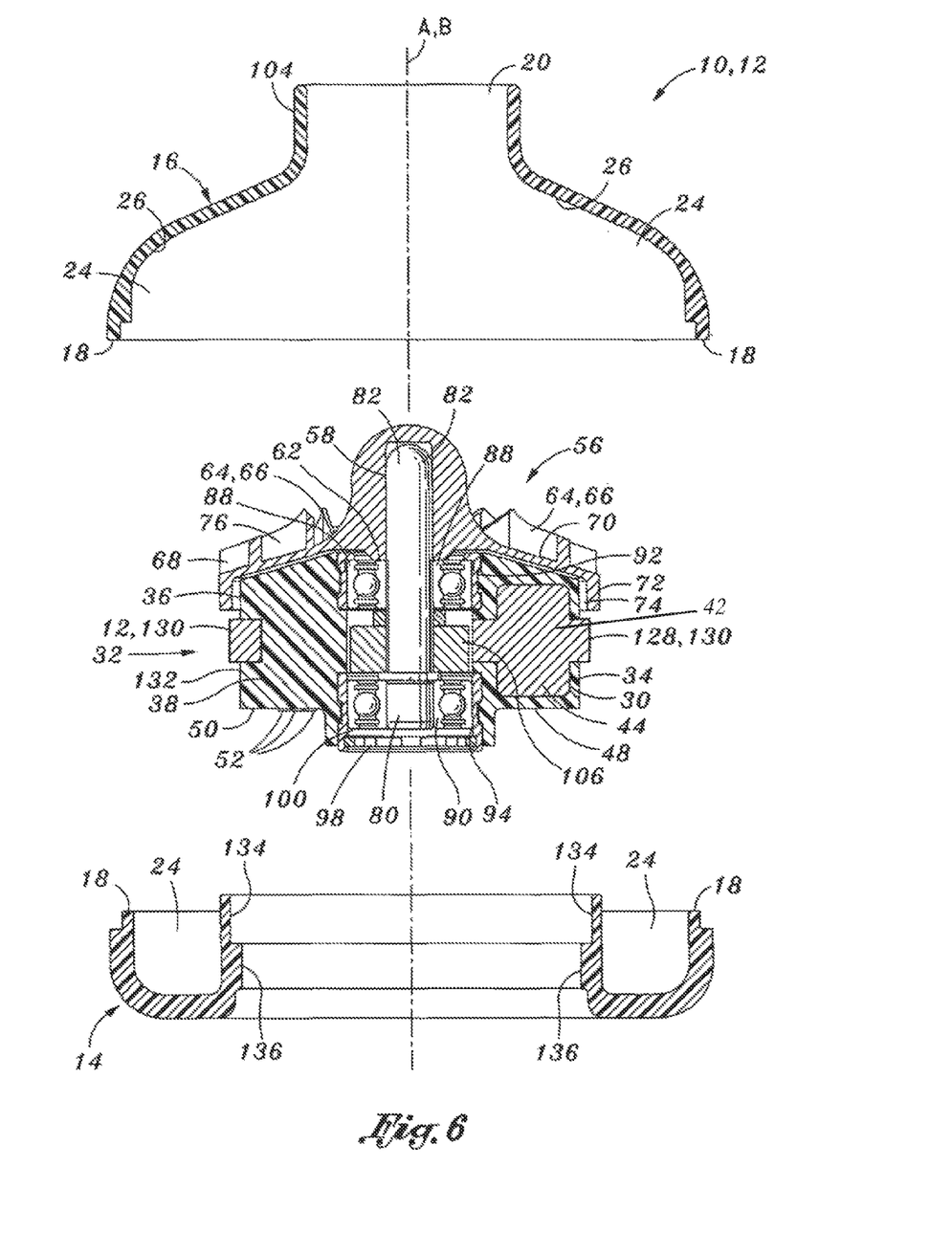
FIG. 6 is an exploded sectional view of the modular compressor assembly illustrating the locating ring configured to be engageable to the annular groove and further illustrating the interconnectivity of the lower and upper housing portions along a perimeter joint.

In this regard, the configuration shown in FIGS. 1 and 6 illustrates an arrangement wherein the rotor magnet 106 is disposed radially inwardly from the stator assembly 32 as opposed to the configuration shown in commonly-owned U.S. Pat. No. 7,012,346, issued to Hoffman et al, the entire contents of which is incorporated by reference herein, wherein the rotor magnet assumes a ring shape which is disposed radially outboard of the stator assembly.

Referring still to FIGS. 1 to 6, the modular compressor assembly 10 further comprises an impeller 56 which is configured to be mountable to and rotatable with the rotor magnet 106. The impeller 56 is fixably mounted onto a motor shaft 78 such as by press fit or other suitable means. The impeller 56 rotates with the rotor magnet 106 which is coupled to the stator assembly 32 by upper and lower bearings 88, 90.

Figure 5:
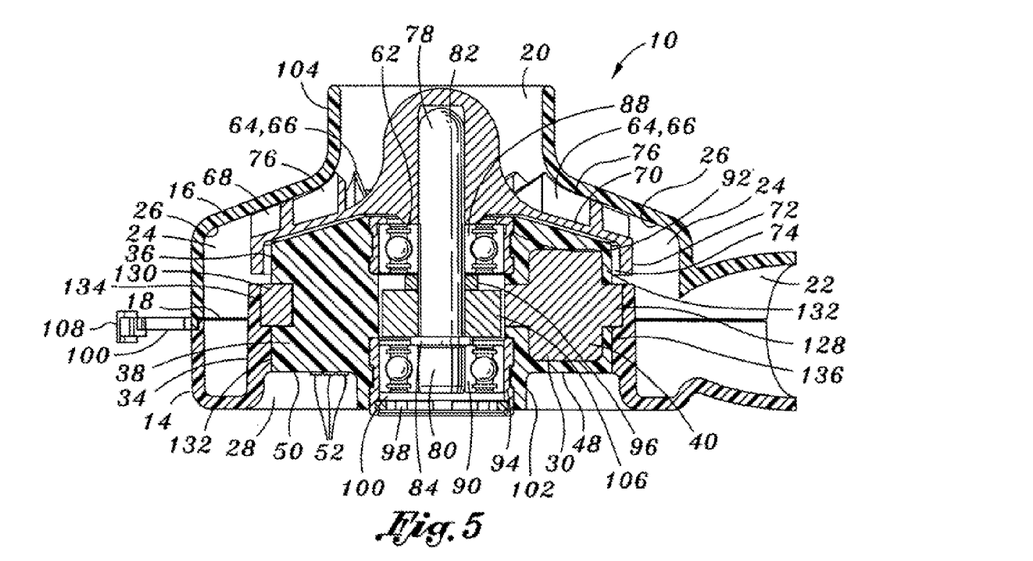
FIG. 5 is a cross-sectional view of the modular compressor assembly taken along lines 5-5 of FIG. 4 and illustrating a locating ring formed on a stator housing and an annular groove formed in the blower housing.

The impeller 56 draws air into an annular blower inlet 20 which is collectively defined by an upper housing neck 104 and a hub portion 60 of the impeller 56 as best seen in FIG. 5. Air drawn into the blower inlet 20 is directed downwardly in an axial direction whereafter the vanes 64, 66 compress the air as the air moves laterally outwardly along vane passages defined by the vanes 64, 66. The compressed air is forced into the annular chamber 24 or volute which is defined by the blower housing 12. The compressed air is then discharged from the blower housing 12 at a blower outlet 22 which is preferably located on a peripheral edge of the blower housing 12.

In one embodiment, the motor assembly 30 is configured as a three-slot/two-hole brushless D.C. motor assembly 30 wherein each of the slots of the stator assembly 32 is arranged circumferentially and defines a number of rotor teeth or core sections 42. Each of the core sections 42 has layers of electrical winding wound thereabout. It should be pointed out that the stator assembly 32 is not limited to the three-slot arrangement illustrated in the figures but may be provided with any number of slots (i.e., core sections 42) with the rotor magnet 106 being provided with a complimentary number of poles. In addition, the motor assembly 30 may be provided in a conventional brushed configuration.

The brushless D.C. motor assembly 30 preferably includes an intelligent electronic controller or commutator 50 which is operative to sequentially commutate or provide current to the core sections 42 of the stator assembly 32 at the appropriate time to induce and maintain rotation of the rotor magnet 106 and, hence, the impeller 56. In this regard, the motor assembly 30 may further include a means for sensing the position and/or orientation of magnetic poles 46 of the rotating rotor magnet 106. For example, position sensors 48 such as Hall sensors may be included in the motor assembly 30 and which are configured to cooperate with the electronic controller to regulate the speed of the motor assembly 30.

Figure 3:
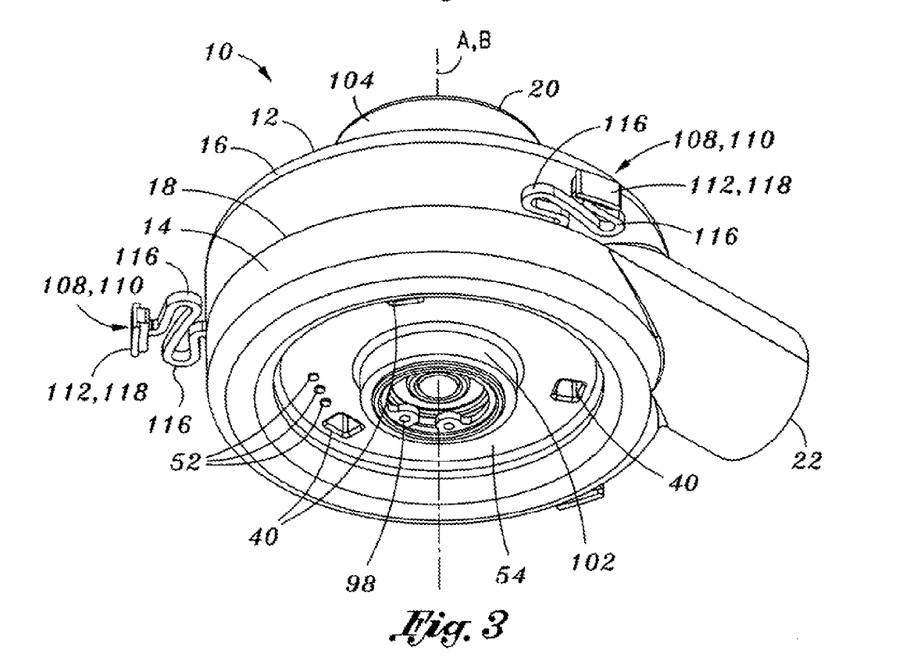
FIG. 3 is a perspective view of the modular compressor assembly looking at an underside thereof.

Referring briefly to FIGS. 3 and 5, the electronic controller may be mounted on a printed circuit board (PCB 54) and may include electrical contacts 52 for connecting to and controlling the motor assembly 30. The controller may further be integrated with the PCB 54 which itself may further include the position sensors 48 (e.g., Hall sensors) to sense the relative positions and speed of the magnetic poles 46 of the rotating rotor magnet 106 relative to the stator assembly 32. The PCB 54 may be located within an annular recess 28 disposed on an underside of the motor assembly 30 and which is collectively defined by a lower housing portion 14 and the stator housing 34 as best seen in FIGS. 3 and 5.

Referring to FIGS. 1, 5 and 6, the compressor assembly 10 further comprises the blower housing 12 which is selectable from among a plurality or variety of different blower housings 12 each having a different cross-sectional geometry, shape or size. As can be seen in FIG. 1, the blower housing 12 may be comprised of upper and lower housing portions 16, 14 which are configured to be engageable to one another such as along a perimeter joint 18 as best seen in FIGS. 5 and 6. More specifically, the upper and lower housing portions 16, 14 may be secured to one another along the perimeter joint 18 such as by adhesive bonding, sonic welding or any other suitable means including mechanical securement.

The upper and lower housing portions 16, 14 are preferably formed as separate components from the motor assembly 30 in order to provide the modular aspect to the compressor assembly 10. In this regard, the upper and lower housing portions 16, 14 may be provided in a variety of different configurations but which are each configured to be engageable to the single, common motor assembly 30 such that the compressor assembly 10 is capable of providing different flow profiles as is required for different patients and different types of treatment.

Toward this end, the impeller 56 is selectable from among a plurality of different impeller 56 configurations. Each impeller 56 configuration is formed complimentary to a set of upper and lower housing portions 16, 14 in order to achieve the desired flow characteristics (i.e., flow rate and/or pressure) with maximum compressive efficiency. Further facilitating the modular aspect of the compressor assembly 10 is the exteriorly accessible location of the PCB 54 on the underside of the blower housing 12. The accessible location of the PCB 54 allows for convenient substitution of the electronic controller and/or commentator with electronic components having operating characteristics that are complimentary to the particular impeller 56 and blower housing 12 combination.

Referring still to FIGS. 1, 5 and 6, mating of the blower housing 12 to the common motor assembly 30 is facilitated by the engagement mechanism 128 which is disposed on the stator housing 34 and/or the blower housing 12. As will be described in greater detail below, the engagement mechanism 128 may be integrally formed in at least one of the stator assembly 32 and/or upper and lower housing portions 16, 14. Each one of the stator assembly 32 and/or upper and lower housing portions 16, 14 may be fabricated as separate components by injection molding or other suitable manufacturing or molding process.

The stator assembly 32 may be constructed of a plurality of core sections 42 and associated electrical windings 44 integrally molded into the stator housing 34. Housing apertures 40 may be strategically placed in the stator assembly 32 to eliminate warpage that may otherwise occur due to uneven shrinkage or contraction during cooling of the injection molded stator assembly 32. In this manner, the molded parts may be fabricated with precise dimensional control which facilitates final assembly of the compressor assembly 10 and allows for extremely close operational tolerances that contribute to the efficiency of the modular compressor assembly 10.

Furthermore, precise control of the dimensional characteristics of the compressor assembly 10 facilitates assembly of the individual components such as bonding of the upper and lower housing portions 16, 14 at the perimeter joint 18. In addition, precise dimensional control of the motor assembly 30 and the blower housing 12 maintains the relatively narrow air gap 76 between the rotating impeller 56 and the housing interior surface 26 during the relatively high speeds (e.g., up to 35,000 RPM) at which the impeller 56 may rotate.

Referring particularly to FIG. 5, the bearing assembly 86 may be integrated into the manufacturing process of the stator assembly 32 wherein upper and lower bearing carriers 92, 94 are integrally molded with the stator assembly 32. As can be seen in FIG. 5, the upper and lower bearing carriers 92, 94 are preferably disposed in spaced relation at upper and lower ends of the stator assembly 32. In consideration of the modular aspect of the compressor assembly 10, the upper and lower bearings 88, 90 are preferably over-sized considering the relatively low inertial and rotational loads imposed thereupon at low flow rates and pressures.

However, by providing the upper and lower bearings 88, 90 in a relatively large size reduces wear of the bearings over time such that the useful life of the compressor assembly 10 is extended. Furthermore, the use of over-sized upper and lower bearings 88, 90 facilitates the substitution of a larger impeller 56 as may be required for increased flow capacity of the compressor assembly 10. Even further, the use of over-sized upper and lower bearings 88, 90 minimizes losses in compressive efficiency and also minimizes the development of vibration and/or noise over time due to normal wear and tear.

Referring briefly to FIGS. 3 and 5, assembly and disassembly of the compressor assembly 10, as may be required for repair or periodic maintenance, is facilitated by the removability of the bearing assembly 86 and rotor magnet 106 from an underside of the stator assembly 32. In one embodiment, the stator assembly 32 may include a retainer element 98 such as a simple snap ring which is engageable to a corresponding groove formed in a lower housing flange 102. As best seen in FIG. 3, the lower housing flange 102 extends axially downwardly from the lower housing portion 14 and the snap ring is engageable into the groove formed therein. The motor assembly 30 preferably includes a biasing element 100 interposed between the retainer element 98 and the lower bearing 90 in order to upwardly bias the bearing assembly 86, rotor magnet 106 and, motor shaft 78 and thereby minimize the air gap 76 between the free edges 68 of the impeller 56 and the housing interior surface 26.

The biasing element 100 may be configured as a wave spring, a compression spring or any other suitable biasing configuration. The biasing element 100 bears against the retainer element 98 (i.e., snap ring) and pushes upwardly against an outer bearing race of the lower bearing 90 such that the lower bearing 90 is biased upwardly against the upper bearing carrier 92. Each one of the upper and lower bearings 88, 90 is comprised of inner and outer bearing races which are interconnected by a plurality of ball bearings.

As best seen in FIG. 5, the motor shaft 78 defines a shaft axis B and includes distal and proximal ends 80, 82. A shaft shoulder 84 is formed adjacent the distal end 80 of the motor shaft 78 to provide a surface against which the rotor magnet 106 may bear on one side of the shaft shoulder 84 and against which the lower bearing 90 assembly 86 may bear against an opposing side of the shaft shoulder 84. A spacer 96 may be interposed between the rotor magnet 106 and the upper bearing 88 assembly to maintain spacing between the upper and lower bearings 88, 90. More specifically, the spacing between the upper and lower bearings 88, 90 is maximized in order to better maintain coaxial alignment of the motor shaft 78 axis with a stator axis A of the stator assembly 32.

Referring to FIGS. 5 and 6, the impeller 56 is adapted to be mounted on a proximal end 82 of the motor shaft 78. The impeller 56 includes a rounded or dome-shaped hub portion 60 having an impeller bore 58 extending at least partially therethrough. A conically shaped ramp portion 70 extends circumferentially around the hub portion 60. The hub portion 60 is disposed in close rotating relationship with an upper surface of the stator assembly 32 in order to minimize total volume occupied by the impeller.

As best seen in FIGS. 1, 5 and 6, the impeller 56 includes a plurality of the vanes 64, 66 extending upwardly from the ramp portion 70. The vanes 64, 66 are disposed in spaced relation to one another on the ramp portion 70 and are preferably non-radially oriented. The vanes 64, 66 define vane passages. As illustrated, the vanes 64, 66 are shown as being generally aft facing in that the outer edges of the vanes point in a direction opposite the rotational direction of the impeller 56.

In one embodiment, the vanes 64, 66 alternate between full-length vanes 66 and partial-length vanes 64 to minimize the generation of pressure pulsations at the outer perimeter which can otherwise occur in relatively small blowers having a limited quantity of vanes 64, 66. However, the alternating partial length and full-length vanes 64, 66 maximize the overall area at the blower inlet 20 while minimizing the generation of pressure pulses at the downstream end of the vanes 64, 66 due to the effective increase in the vane quantity at the outlet end of the vane passages.

Each one of the vanes 64, 66 defines a free edge 68 which is sized and configured complimentary to the housing interior surface 26 such that the impeller 56 rotates in extremely close proximity thereto in order to minimize the generation of energy-reducing fluid eddies or turbulence. Such eddies may be characterized as aerodynamic or parasitic energy losses which otherwise occur in conventional centrifugal blowers of the prior art. As is known in the art, parasitic fluid eddies limit the pressure and flow rate capability of centrifugal blowers and can also contribute to the generation of unwanted acoustic energy(i.e., noise) by the compressor assembly 10.

However, depending upon the particular configurations of the impeller 56 and blower housing 12 as used in conjunction with the common motor assembly 30, the height of the vanes 64, 66 is preferably optimized for the pressure and flow rate of the compressor assembly 10. Due to the optimized vane height and extremely small air gap 76 between the free edges 68 of the vanes 64, 66 and the housing interior surface 26, the compressor assembly 10 is capable of effectively producing the desired flow rate and pressure output with minimum input power at the motor assembly 30 and minimal generation of noise and vibration.

Referring to FIGS. 5 and 6, assisting in maintaining the air gap 76 between the vanes 64, 66 and the blower housing 12 is the dimensional precision with which the impeller 56 is fabricated. More specifically, the impeller 56 is preferably statically and dynamically balanced by removing material from the downwardly turned lip portion 72 of the impeller. As best seen in FIG. 5, the lip portion 72 extends about a perimeter of the ramp portion 70 and is configured to fit within an annular undercut 36 formed along an upper perimeter edge of the stator housing 34. The annular undercut 36 and lip portion 72 collectively define a narrow lip gap 74 which allows the outer surface of the lip portion 72 to lie generally flush with the outer wall 132 of the stator housing 34.

Referring to FIGS. 1, 5 and 6, the precise geometric relationship between the motor assembly 30 and the blower housing 12 is facilitated by the engagement mechanism 128 which is disposed on the stator housing 34 and/or the blower housing 12. As was earlier mentioned, the engagement mechanism 128 allows for interchangeable mounting of different blower housing 12 configurations with the common motor assembly 30 in order to achieve different flow characteristics of the compressor assembly 10. In one embodiment, the engagement mechanism 128 may be integrated into the lower housing portion 14 and the stator housing 34.

The engagement mechanism 128 may be embodied as a locating ring 130 extending about a circumference of an outer wall 132 of the stator housing 34. A complimentary annular groove 134 may be formed on an inner wall 135 of the lower housing portion 14 and is preferably sized and configured to receive the locating ring 130 therewithin. Although shown as a contiguous circumferential ring element, the locating ring 130 may be provided in a variety of alternative shapes, sizes and configurations. For example, the locating ring 130 may be comprised of a plurality of angularly spaced ring segments disposed around the outer wall 132 of the stator housing 34. In another configuration, the engagement mechanism 128 may be configured as a plurality of angularly spaced bosses extending outwardly from the outer wall 132 of the stator housing 34. The inner wall 136 of the lower housing portion 14 preferably includes complimentary features configured to receive and/or engage the features formed on the outer wall 132 of the stator housing 34.

The modular aspect of the compressor assembly 10 provides a convenient means for interchangeability of blower housing 12 configurations with the common motor assembly 30. For example, FIGS. 5 and 6 illustrate different blower housing 12 configurations mounted on the common motor assembly 30. More specifically, the common motor assembly 30 illustrated in FIG. 5 has the same overall configuration (i.e., same size and shape) as the common motor assembly 30 illustrated in FIG. 6 although the blower housing 12 in FIG. 6 is of a larger size (i.e., larger outer diameter) than the blower housing 12 illustrated in FIG. 5. Because of the size and configuration differences in the blower housings 12, the compressor assemblies in FIGS. 5 and 6 are capable of different flow rates. Preferably, each of the blower configurations is optimized for use with patients having different respiratory needs.

Figure 2:
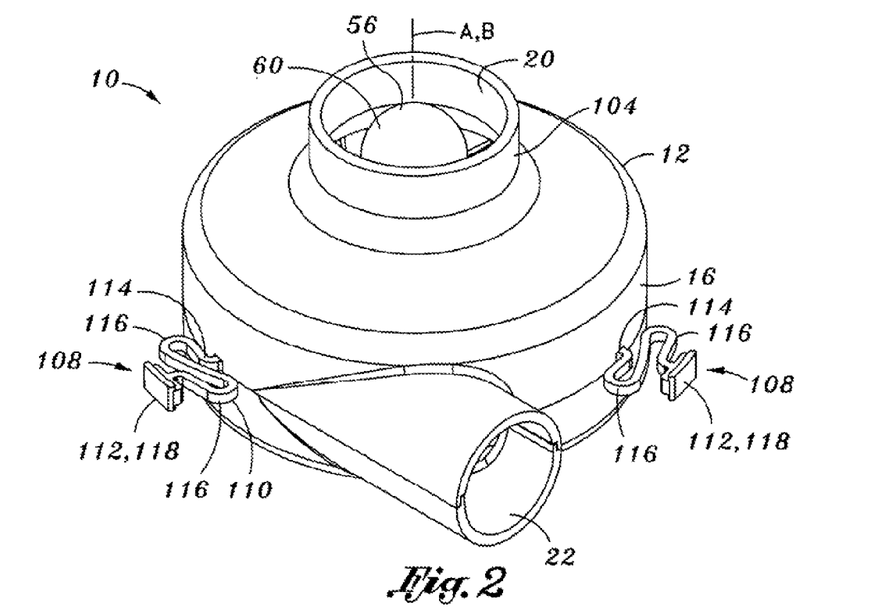
FIG. 2 is a perspective view of the modular compressor assembly in an assembled state.
Figure 4:
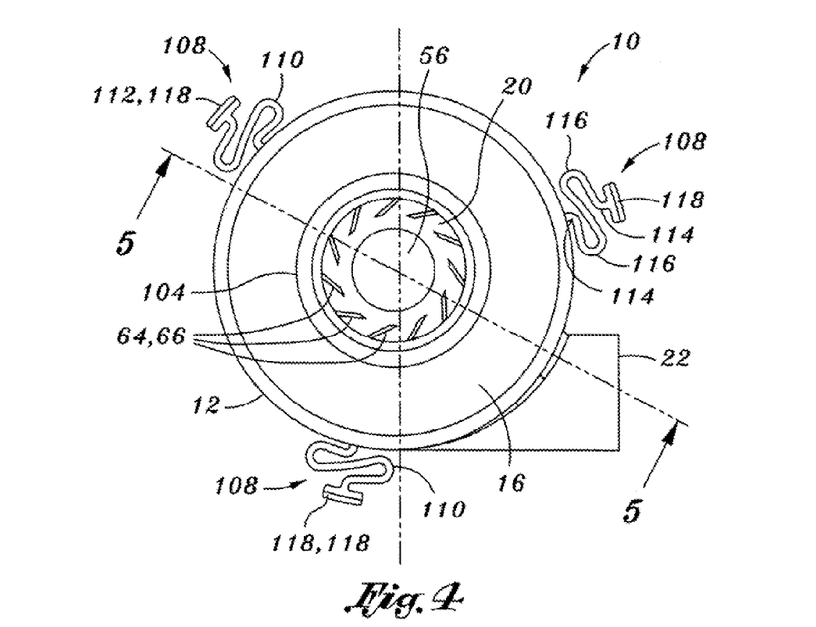
FIG. 4 is a top view of the modular compressor assembly.

Referring briefly to FIGS. 2 to 4, the blower housing 12 may optionally include at least one and, more preferably, three angularly spaced suspension mounts 108 extending laterally outwardly from at least one of the upper and lower housing portions. The suspension mounts 108 are sized and configured to support the compressor assembly 10 while attenuating or dampening vibration (e.g., radial or axial) generated by the compressor assembly 10. Preferably, the suspension mounts 108 are located adjacent to the perimeter joint 18 and are configured to prevent or mitigate propagation of vibration from the compressor assembly 10 to a mounting frame 120 or housing.

Each of the suspension mounts 108 is preferably configured as a serpentine-shaped spring member 110 which has a terminus end 112 preferably adapted to mount the compressor assembly 10 to mounting slots formed in a mounting frame or housing. Each of the terminus ends 112 of the spring member 110 preferably includes a generally axially-oriented tab member 118. Each one of the spring members 110 extends laterally outwardly from the blower housing 12 wherein the spring member 110 forms a 90° bend 114. The spring member 110 may also include a pair of 180° bends 116 prior to terminating at an additional 90° bend 114 at the terminus end 112 of the spring member. However, any number of turns may be included in the spring member 110 in order to provide the desired dampening or attenuating characteristics.

Referring briefly to FIG. 1, also included in the present invention is a method of constructing a modular compressor assembly 10. The method comprises the steps of forming a stator assembly 32 having upper and lower bearing carriers 92, 94 and a plurality of core sections 42. As was earlier mentioned, each one of the core sections 42 preferably extends radially outwardly from the stator bore 38 and includes a winding to allow for sequential magnetization of the core sections 42 and rotation of the motor assembly 30.

The method further comprises molding the stator housing 34 to include the stator bore 38 such that the stator housing 34 encapsulates the stator assembly 32 and coaxially confines the upper and lower bearing carriers 92, 94 relative to the stator bore 38. The stator bore 38 defines the stator axis A. The method further comprises forming the motor shaft 78 which preferably includes the shaft shoulder 84 located on a distal end 80 thereof. The rotor magnet 106 is preferably fixably mounted to the motor shaft 78 such that the rotor magnet 106 is disposed in abutting contact with the shaft shoulder 84. Assembly of the motor shaft 78 may further include installation of the spacer 96 followed by mounting of the upper bearing 88.

The upper bearing 88, spacer 96 and rotor magnet 106 are insertable into the stator bore 38 such as from an underside of the compressor assembly 10 as best seen in FIG. 2. The lower bearing 90 is preferably installed on the motor shaft 78 and placed in abutting contact with an underside of the shaft shoulder 84. The biasing element 100 and retainer element 98 are then installed within the lower housing flange 102 as best seen in FIGS. 3 and 5. The method further comprises securing the impeller 56 on the proximal end 82 of the motor shaft 78 such as by press fit until a mounting boss 62 of the impeller 56 is in abutting contact with the upper bearing 88. Position sensors 48 (e.g., Hall sensors), PCB 54 and other electronic components may be installed on the underside of the motor assembly 30 as shown in FIG. 3.

Importantly, the method further includes forming the engagement mechanism 128 on at least one of the stator housing 34 and the blower housing 12. For example, the engagement mechanism 128 may be formed by forming the locating ring 130 on the outer wall 132 of the stator housing 34 as best seen in FIG. 1. The step of forming the engagement mechanism 128 may further comprise forming the annular groove 134 on the inner wall 136 of the lower housing portion 14 wherein the annular groove 134 is sized and configured complimentary to the locating ring 130 on the stator housing 34.

The method of constructing the compressor assembly 10 may include mating the lower housing portion 14 to the stator housing 34 by engaging the locating ring 130 to the annular groove 134. As mentioned above, the engagement mechanism 128 is not limited to the locating ring 130 but may take a variety of alternative configurations including ring segments, or other mechanical features. The construction of the compressor assembly 10 may include the step of statically and dynamically balancing the impeller 56 such that the air gap 76 between the free edges 68 of the vanes 64, 66 and the housing interior surface 26s is preferably maintained at less than approximately 0.006 inches and, more preferably, at approximately 0.002 inches. Following the balancing of the impeller, the upper housing portion 16 may be secured to the lower housing portion 14 at the perimeter joint 18 by any suitable means such as adhesive bonding, sonic welding or mechanical attachment. The upper and lower housing portions 16, 14 collectively define the annular chamber 24 (i.e., volute).

The description of the various embodiments of the present invention are presented herein to illustrate preferred embodiments of the invention and other inventive concepts as may be otherwise variously embodied and employed. The claims are intended to be construed to include such variations except insofar as limited by the prior art.

What is claimed is:

1. A method of constructing a modular compressor assembly, comprising:
    forming a stator assembly having upper and lower bearing carriers and at least one core section having a winding extending therearound, the upper and lower bearing carriers being separated by a gap configured to receive a rotor magnet;
    molding a stator housing with a stator bore such that the stator housing encapsulates the stator assembly and coaxially confines the upper and lower bearing carriers relative to the stator bore; and
    forming a locating ring on an outer wall of the stator housing, wherein the locating ring comprises a polygon cross-section.

2. The method of claim 1, further comprising:
    forming a motor shaft; and
    mounting the rotor magnet on the motor shaft, wherein the stator assembly and rotor magnet collectively define a motor assembly.

3. The method of claim 2, further comprising:
    disposing upper and lower bearings between the motor shaft and the upper and lower bearing carriers such that the motor shaft is coaxial with the stator bore.

4. The method of claim 2, further comprising:
    forming an impeller having a plurality of elongate vanes each defining a vane height and having a free edge; and
    securing the impeller to the motor shaft.

5. The method of claim 1, further comprising:
    forming a lower housing portion having an engagement mechanism configured to facilitate removable engagement of the lower housing portion to the stator housing.

6. The method of claim 5, further comprising:
    mating the lower housing portion to the stator housing by engaging the locating ring to an annular groove on an inner wall of the lower housing portion.

7. The method of claim 5, further comprising:
    securing the lower housing portion to the stator housing; and
    forming an upper housing portion configured to mate to the lower housing portion.

8. The method of claim 7, further comprising:
securing the upper housing portion to the lower housing portion such that the upper and lower housing portions collectively define an annular chamber having a housing interior surface.

9. The method of claim 1, further comprising:
forming an annular groove on an inner wall of the lower housing portion, the annular groove being formed complementary to the locating ring.

* * * * *